(12) United States Patent
Gebhardt et al.

(10) Patent No.: US 9,096,570 B2
(45) Date of Patent: Aug. 4, 2015

(54) PROCESS FOR MANUFACTURING SUBSTITUTED 3-PYRIDYLMETHYL AMMONIUM BROMIDES

(75) Inventors: Joachim Gebhardt, Wachenheim (DE); Frederik Menges, Schriesheim (DE); Michael Rack, Eppelheim (DE); Michael Keil, Freinsheim (DE); Jochen Schroeder, Lambsheim (DE); Stefan Orsten, Ellerstadt (DE); Helmut Zech, Bad Duerkheim (DE); David Cortes, Quincy, IL (US); Robert Leicht, Hannibal, MO (US); Tony Yegerlehner, Palmyra, MO (US); Rodney F. Klima, Quincy, IL (US)

(73) Assignee: BASF SE, Ludwigshafen (DE)

( * ) Notice: Subject to any disclaimer, the term of this patent is extended or adjusted under 35 U.S.C. 154(b) by 349 days.

(21) Appl. No.: 13/128,787

(22) PCT Filed: Nov. 13, 2009

(86) PCT No.: PCT/EP2009/065155
§ 371 (c)(1),
(2), (4) Date: May 11, 2011

(87) PCT Pub. No.: WO2010/055139
PCT Pub. Date: May 20, 2010

(65) Prior Publication Data
US 2011/0224433 A1   Sep. 15, 2011

Related U.S. Application Data

(60) Provisional application No. 61/114,230, filed on Nov. 13, 2008.

(51) Int. Cl.
C07D 401/06 (2006.01)
C07D 403/06 (2006.01)
C07D 413/06 (2006.01)
C07D 417/06 (2006.01)
C07D 213/80 (2006.01)
C07D 401/04 (2006.01)

(52) U.S. Cl.
CPC ............ C07D 401/04 (2013.01); C07D 213/80 (2013.01); C07D 401/06 (2013.01); C07D 403/06 (2013.01); C07D 413/06 (2013.01); C07D 417/06 (2013.01)

(58) Field of Classification Search
CPC .. C07D 213/60; C07D 213/79; C07D 213/81; C07D 213/84; C07D 401/04; C07D 401/06; C07D 401/14; C07D 403/06; C07D 403/14; C07D 413/06; C07D 413/14; C07D 417/06; C07D 417/14
USPC ........ 546/268.1, 274.1, 310, 321, 255, 269.7, 546/271.4, 272.7, 304, 323, 326, 345
See application file for complete search history.

(56) References Cited

U.S. PATENT DOCUMENTS

| 5,026,859 | A |   | 6/1991 | Finn |
| 5,288,866 | A | * | 2/1994 | Strong .......................... 544/215 |
| 5,334,576 | A |   | 8/1994 | Doehner, Jr. et al. |
| 5,378,843 | A |   | 1/1995 | Strong |
| 5,545,835 | A | * | 8/1996 | Strong .......................... 544/215 |
| 5,760,239 | A |   | 6/1998 | Wu |

FOREIGN PATENT DOCUMENTS

| DE | 3330604 | 3/1985 |
| EP | 0144595 | 6/1985 |
| EP | 0184027 | 6/1986 |
| EP | 0 539 676 | 5/1993 |
| EP | 0 548 532 | 6/1993 |
| EP | 0 747 360 | 12/1996 |
| EP | 0 322 616 | 4/1997 |
| EP | 0 933 362 | 8/1999 |
| JP | 62-174069 | 7/1987 |
| WO | WO 2010/054952 | 5/2010 |
| WO | WO 2010/054954 | 5/2010 |
| WO | WO 2010/055042 | 5/2010 |
| WO | WO 2010/006668 | 6/2010 |

OTHER PUBLICATIONS

Zubrik, James. W., "The Organic Chem Lab Survival Guide", copyright 1984, 1988, by John Wiley & Sons, Inc.
Office Action dated Sep. 17, 2012, in U.S. Appl. No. 13/128,779, filed May 11, 2011.
International Search Report prepared in International Application No. PCT/EP2009/065155, filed Nov. 13, 2009.
International Preliminary Report on Patentability from corresponding International Application No. PCT/EP2009/065155, filed Nov. 13, 2009.
Bi, Q. et al., "Review on Synthesis of Imazamox", Modern Agrochemicals, vol. 6, No. 2, (2007), pp. 10-14.
Tagawa, Y. et al., "Reinvestigation of nitrosation of methlypyridines and their 1-oxides and deoxygenation of 3-pyridinecarbaldehyde 1-oxide oxime", Heterocycles, (1992), pp. 1605-1612, vol. 34, No. 8.

* cited by examiner

*Primary Examiner* — Venkataraman Balasubramanian
(74) *Attorney, Agent, or Firm* — Brinks Gilson & Lione

(57) ABSTRACT

A process for manufacturing 5,6-disubstituted-3-pyridylmethyl ammonium bromides (I),

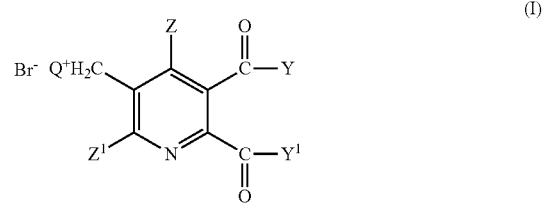

wherein
Q is a tertiary aliphatic or cyclic, saturated, partially unsaturated or aromatic amine;
Z is hydrogen or halogen;
$Z^1$ is hydrogen, halogen, cyano or nitro;

Y and $Y^1$ are each independently $OR^1$, $NR^1R^2$, or when taken together $YY^1$ is —O—, —S— or $NR^3$—;

$R^1$ and $R^2$ are each independently hydrogen, $C_1$-$C_4$ alkyl optionally substituted with $C_1$-$C_4$ alkoxy or phenyl optionally substituted with one to three $C_1$-$C_4$ alkyl groups, $C_1$-$C_4$ alkoxy groups or halogen atoms, or phenyl optionally substituted with one to three $C_1$-$C_4$ alkyl groups, $C_1$-$C_4$ alkoxy groups or halogen atoms;

$R^3$ is hydrogen or $C_1$-$C_4$ alkyl;

comprises the steps of (i) reacting a compound of formula (II),

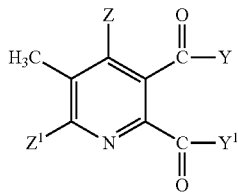

(II)

wherein the symbols have the meaning given in formula (I), with bromine in the presence of a radical initiator in a solvent mixture comprising an aqueous phase and an organic phase, where the organic phase comprises a solvent selected from 1,2-dichloroethane, chlorobenzene, 1,2-dichlorobenzene, 1,3-dichlorobenzene, 1,4-dichlorobenzene and tetrachloromethane, and where the pH-value of the aqueous phase is from 3 to <8, to obtain a 3-bromomethyl-5,6-disubstituted pyridine compound (III),

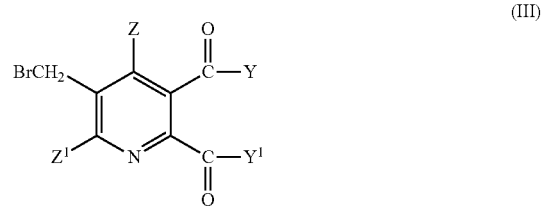

(III)

wherein Y, $Y^1$, Z and $Z^1$ have the meanings given in formula (I), and (ii) reacting the bromo compound of formula (III) with a tertiary amine base Q in a solvent at a temperature range of about 0° C. to 100° C.

15 Claims, No Drawings

PROCESS FOR MANUFACTURING SUBSTITUTED 3-PYRIDYLMETHYL AMMONIUM BROMIDES

This application is a National Stage application of International Application No. PCT/EP2009/065155, filed Nov. 13, 2009, which claims the benefit of U.S. Provisional Application No. 61/114,230 filed Nov. 13, 2008, the entire contents of which are hereby incorporated herein by reference.

The invention relates to a process for manufacturing 3-pyridylmethyl ammonium bromides and further conversion of these compounds to herbicidal 5-substituted-2-(2-imidazolin-2-yl)nicotinic acids, such as imazamox.

Derivatives of 2-(2-imidazolin-2-yl)nicotinic acids, like imazamox (2-[(RS)-4-isopropyl-4-methyl-5-oxo-2-imidazolin-2-yl]-5-methoxymethylnicotinic acid),

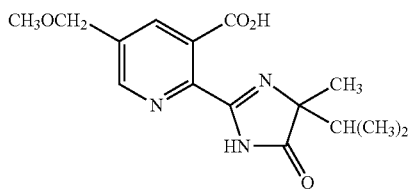

are useful selective herbicides which act as ALS-inhibitors and can be used in pre- and post-emergence applications.

Various processes for the synthesis of these compounds are known from the literature, see e.g. EP-A 0 322 616, EP-A 0 747 360, EP-A 0 933 362 or Q. Bi et al, Modern Agrochemicals 6(2)(2007) 10-14.

Although synthesis on an industrial scale is carried out by these methods there is still room for improvement, specifically in view of economical and ecological aspects, such as overall yield improvement or the avoidance of certain solvents or reagents.

EP-A 0 548 532 discloses the preparation of 5,6-disubstituted-3-pyridylmethyl ammonium halide compounds by halogenation of the respective 5,6-disubstituted-3-methyl-pyridines and subsequent reaction with a trialkylamine or a cyclic unsaturated or saturated amine.

Halogenating agents proposed in EP-A 0 548 532 include N-bromosuccinimide, 1,3-dibromo-5,5-dimethylhydantoin, bromine, chlorine, t-butylhypochlorite, sulfuryl chloride, sulfuryl bromide, N-chlorosuccinimide and the like; however, all examples are carried out with either N-bromosuccinimide or 1,3-dibromo-5,5-dimethylhydantoin.

One task of the invention is to provide an improved process for the halogenation of 5,6-disubstituted-3-methyl-pyridines. A further task of the invention is to provide an improved process for producing 5,6-disubstituted-3-pyridylmethyl ammonium bromides (I) and further conversion of these compounds to herbicidal 2-(2-imidazolin-2-yl)nicotinic acids or derivatives thereof.

It has been found that the bromination of 5,6-disubstituted-3-methylpyridines and further reaction with an amine can be significantly improved by using specific solvents and bromine as bromination agent in a two-phase system with water.

DE-A 33 30 604 discloses a process for preparing bromomethylthiophen carboxylic esters by bromination of the methyl compound with bromine under irradiation in a two-phase system comprising water and a fluorochlorohydrocarbon. However, this reference does not disclose the specific educts, solvents and reaction conditions of the invention.

Accordingly, in one aspect of the invention there is provided a process for manufacturing 5,6-disubstituted-3-pyridylmethyl ammonium bromides (I),

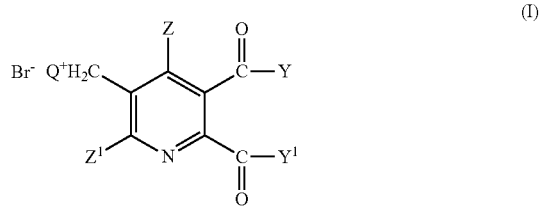

wherein

Q is a tertiary aliphatic or cyclic, saturated, partially unsaturated or aromatic amine;

Z is hydrogen or halogen;

$Z^1$ is hydrogen, halogen, cyano or nitro;

Y and $Y^1$ are each independently $OR^1$, $NR^1R^2$, or when taken together $YY^1$ is —O—, —S— or $NR^3$—;

$R^1$ and $R^2$ are each independently hydrogen,
$C_1$-$C_4$ alkyl optionally substituted with $C_1$-$C_4$ alkoxy or phenyl optionally substituted with one to three $C_1$-$C_4$ alkyl groups, $C_1$-$C_4$ alkoxy groups or halogen atoms, or phenyl optionally substituted with one to three $C_1$-$C_4$ alkyl groups, $C_1$-$C_4$ alkoxy groups or halogen atoms;

$R^3$ is hydrogen or $C_1$-$C_4$ alkyl;

comprising the steps of (i) reacting a compound of formula (II),

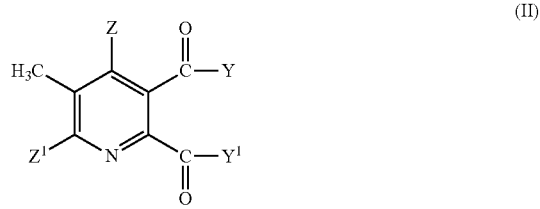

wherein the symbols have the meaning given in formula (I), with bromine in the presence of a radical initiator in a solvent mixture comprising an aqueous phase and an organic phase, where the organic phase comprises a solvent selected from 1,2-dichloroethane, chlorobenzene, 1,2-dichlorobenzene, 1,3-dichlorobenzene, 1,4-dichlorobenzene and tetrachloromethane, and where the pH-value of the aqueous phase is from 3 to <8, to obtain a 3-bromomethyl-5,6-disubstituted pyridine compound (III),

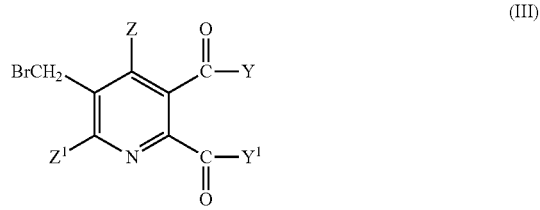

wherein Y, $Y^1$, Z and $Z^1$ have the meanings given in formula (I), and (ii) reacting the bromo compound of formula (III) with a tertiary amine Q in a solvent at a temperature range of about 0° C. to 100° C.

In a further aspect of the invention there is provided a process for manufacturing a 5,6-disubstituted-3-methoxymethylpyridine of formula (IV),

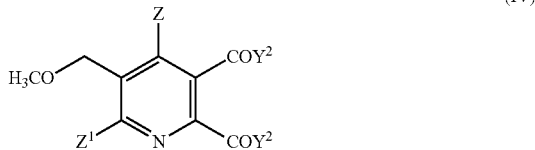

where
$Z^1$ and $Z^2$ are as defined in formula (I) and
$Y^2$ is $OCH_3$ or OM, and
M is an alkaline metal, an alkaline earth metal or H, preferably an alkaline metal or an alkaline earth metal,
comprising the steps of:
(i)/(ii) preparing a 5,6-disubstituted-3-pyridylmethyl ammonium bromide of the formula (I) as described above, and
(iii) reacting the compound of formula (I) in methanol, toluene or methanol/toluene mixtures with a base selected from $MOCH_3$ and MOH (if methanol is a solvent), where M is as defined in formula (IV) and optionally acidifying the obtained product (M=H).

In a further aspect of the invention there is provided a process for preparing a herbicidal imidazolinone compound of formula (V),

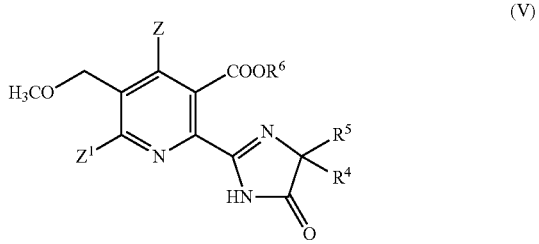

wherein
Z, $Z^1$ are as defined in formula (I);
$R^4$ is $C_1$-$C_4$ alkyl;
$R^5$ is $C_1$-$C_4$ alkyl, $C_3$-$C_6$ cycloalkyl, or $R^4$ and $R^5$, when taken together with the atom to which they are attached, represent a $C_3$-$C_6$ cycloalkyl group optionally substituted with methyl, and
$R^6$ is hydrogen; a group of the formula —N=C(lower alkyl)$_2$; $C_1$-$C_{12}$ alkyl optionally substituted with one of the following groups: $C_1$-$C_3$ alkoxy, halogen, hydroxyl, $C_3$-$C_6$ cycloalkyl, benzyloxy, furyl, phenyl, halophenyl, lower alkylphenyl, lower alkoxyphenyl, nitrophenyl, carboxyl, lower alkoxycarbonyl, cyano or tri lower alkylammonium; $C_3$-$C_{12}$ alkenyl optionally substituted with one of the following groups: $C_1$-$C_3$ alkoxy, phenyl, halogen or loweralkoxycarbonyl or with two $C_1$-$C_3$ alkoxy groups or two halogen groups; $C_3$-$C_6$ cycloalkyl optionally substituted with one or two $C_1$-$C_3$ alkyl groups; or
a cation preferably selected from the group consisting of alkali metals, alkaline earth metals, manganese, copper, iron, zinc, cobalt, lead, silver, nickel, ammonium and organic ammonium;
comprising the steps of:
(i)/(ii)/(iii) preparing a compound of formula (IV) as described above, (iv) converting the compound of formula (IV) into the herbicidal compound of formula (V).

The process of the invention leads to higher yields, higher productivity (higher space time yields, lower fixed costs), lower raw material costs (bromine is cheaper than organic bromination agents like DBDMH) and an improved selectivity for the compounds of formula (I). The organic phase is free of organic byproducts from the bromination agent (e.g. dimethylhydantoine from DBDMH) that have to be separated for example by an additional basic wash. In particular the higher density solvent 1,2-dichloroethane allows to isolate the compounds of formula (I) in a higher concentrated aqueous solution that is free of insoluble impurities.

Preferred are compounds of formula (I) where the symbols have the following meanings:
Z is preferably hydrogen or halogen.
$Z^1$ is preferably hydrogen, halogen, cyano or nitro.
Y and $Y^1$ are preferably each independently $OR^1$ or, when taken together $YY^1$ is preferably O.
$R^1$ is preferably independently hydrogen or $C_1$-$C_4$ alkyl.
$R^3$ is preferably hydrogen or $C_1$-$C_4$ alkyl.
$Q^+$ is preferably

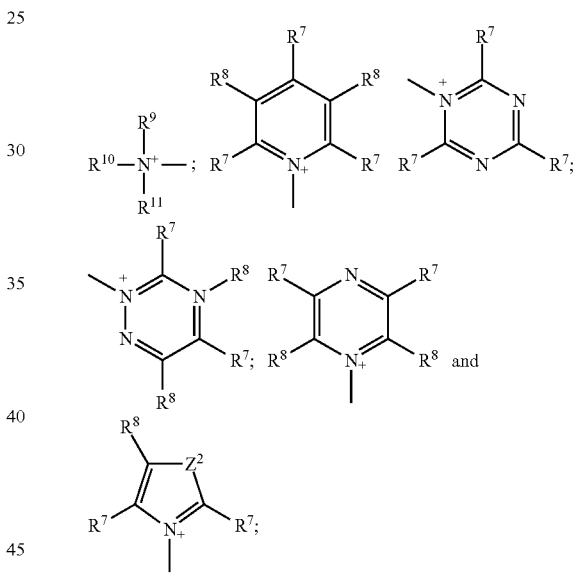

$Z^2$ is O, S or $NR^{12}$;
$R^{12}$ is $C_1$-$C_4$ alkyl;
$R^7$ and $R^8$ are each independently hydrogen, halogen, $C_1$-$C_4$ alkyl or $C_1$-$C_4$ alkoxy, or, when taken together, $R^7$ and $R^8$ form a 5- or 6-membered saturated or unsaturated ring optionally interrupted by O, S, or $NR^{12}$ and optionally substituted with one to three halogen atoms, $C_1$-$C_4$ alkyl groups or $C_1$-$C_4$ alkoxy groups, and
$R^9$, $R^{10}$ and $R^{11}$ are each independently $C_1$-$C_4$ alkyl, or $R^9$ and $R^{10}$, when taken together, form a 5- or 6-membered ring in which $R^9R^{10}$, is represented by the structure: —$(CH_2)_n$—, optionally interrupted by O, S or $NR^9$, where n is an integer of 3, 4 or 5, provided $R^{11}$ is $C_1$-$C_4$ alkyl.

Preferably, all symbols in formula (I) have the preferred meanings.

More preferred are compounds of formula (I) where the symbols have the following meanings:
Z and $Z^1$ are more preferably hydrogen.
Y and $Y^1$ are more preferably $OR^1$.
$R^1$ is more preferably $C_1$-$C_4$ alkyl.

$R^3$ is more preferrably hydrogen or $C_1$-$C_4$ alkyl.

$Q^+$ is more preferably $^\oplus NR^9 R^{10} R^{11}$ or pyridinium.

$R^9$, $R^{10}$ and $R^{11}$ are more preferably each independently $C_1$-$C_4$ alkyl, or $R^9$ and $R^{10}$, when taken together, form a 5- or 6-membered ring in which $R^9 R^{10}$, is represented by the structure: —$(CH_2)_n$—, optionally interrupted by O, S or $NR^{12}$, where n is an integer or 3, 4 or 5, provided $R^{11}$ is $C_1$-$C_4$ alkyl; more preferably $R^9$, $R^{10}$ and $R^{11}$ are $C_1$-$C_4$ alkyl.

More preferred are compounds of formula (I) where all symbols have the more preferred meanings.

Particularly preferred are the compounds of formula (I) where the symbols have the following meanings:

Z and $Z^1$ are particularly preferred hydrogen.

Y and $Y^1$ are particularly preferred $OR^1$.

$R^1$ is particularly preferred $CH_3$.

Q is particularly preferred $^\oplus NR^9 R^{10} R^{11}$ or pyridinium.

$R^9$, $R^{10}$, $R^{11}$ are particularly preferred methyl.

Accordingly, a particularly preferred compound of formula (I) is the compound of formula (Ia):

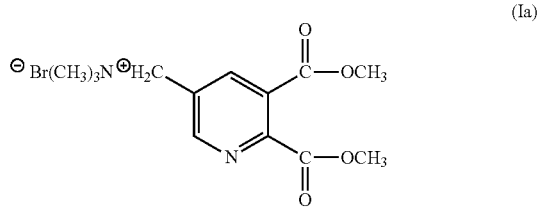

(Ia)

The respective pyridinium compound (Ib) is also particularly preferred.

Preferred, more preferred and particularly preferred compounds of formula (II) are the ones leading to the respective compounds of formula (I).

The compounds of formula (II) and their preparation are known, e.g. from EP-A 0 933 362.

The molar ratio of pyridine compound (II) to bromine is generally in the range of 1:0.5-1.2, preferably 1:0.6-1.0, more preferably 1:0.7-0.95.

It is also possible to work with half the equivalents of bromine, and to generate bromine in the reaction mixture from HBr with an oxidation agent like $H_2O_2$.

Suitable free-radical generators for initiating the reaction are those which decompose at the selected reaction temperature. Examples of preferred initiators are free-radical generators, such as azo compounds and peroxides. It is also possible, however, to use redox systems, especially those based on hydroperoxides, such as cumene hydroperoxide.

Radical initiators suitable for use in the method of the invention include 2,2'-azobisisobutyronitrile, 2,2'-azobis(2-methylbutanenitrile), 2,2'-azobis(2,4-dimethyl-pentanenitrile), 1,1'-azobis(cyclohexanecarbonitrile), organic and inorganic peroxides such as dilauroyl peroxide, hydrogen peroxide, tert-butylperoxy-pivalate, benzoyl peroxide and the like, with 2,2'-azobisisobutyronitrile, 2,2'-azobis(2-methylbutanenitrile) and dilauroyl peroxide being preferred, and with 2,2'-azobisisobutyronitrile and 2,2'-azobis(2-methylbutanenitrile) being particularly preferred.

The molar ration of initiator to bromine is preferably in the range of 0.04-0.15:1, more preferably 0.06-0.10:1.

The organic solvent is selected from the group consisting of 1,2-dichloroethane, chlorobenzene 1,2-dichlorobenzene, 1,3-dichlorobenzene, 1,4-dichlorobenzene and tetrachloromethane, preferably 1,2-dichloroethane and chlorobenzene. 1,2-dichloroethane is particularly preferred. Mixtures, in particular of the dichlorobenzenes, are also possible.

The amount of organic solvent may vary to a large extent. Preferably 900 g to 2000 g, more preferably 1000 g to 1300 g, organic solvent per mol of compound (II) are employed.

The reaction mixture comprises an organic phase and an aqueous phase. The amount of the aqueous phase may vary to a large extent. Preferably 140 g to 500 g, more preferably 140 g to 300 g, particularly 150 g to 200 g of water per mol of the compound of formula (II) are employed.

During the course of the reaction the pH-value of the aqueous phase is kept in the range of from 3 to <8, preferably of from 3 to 7, more preferably of from 4 to 7. Control of the pH-value can be achieved by adding a suitable base, preferably an inorganic base such as a hydroxide of an alkaline metal, e.g. NaOH, or an alkaline earth metal. Aqueous NaOH is a preferred base, particularly in diluted form (e.g. containing 5-20 wt.-% NaOH).

To achieve the desired control of the pH-value the base may be added continuously over the course of the reaction, or the pH-value is checked continuously and base is added by a connected automated dosage device.

In one preferred embodiment step (i) of the reaction is carried out by dissolving the compound (II) in the organic phase and water adding to form the aqueous phase.

The initiator is added as pure compound or in solution, at room temperature (generally a temperature in the range of from 22 to 25° C.) or at reaction temperature after heating. Depending on the initiator decomposition temperature, a part or even the full amount of the initiator have to be added before the start of the bromine dosage. The amount of starter that has to be added during the bromine addition is also depending on the decomposition temperature. A minimum concentration of free radicals should be always available during the bromination reaction.

For 2,2'-azobis(2-methylbutanenitrile) a solution with initiator in an organic solvent is added. Slow addition of bromine as well as the base to control the pH-value can be started at the same time or some time later. It is preferred to start the bromine/base dosage later in order to have a sufficient amount of free radicals in the mixture when the bromination reaction starts. After completion of the reaction the mixture is cooled and the phases are separated.

The reaction is generally carried out at a temperature of about 50° C. to about 120° C., preferably about 60° C. to about 90° C.

The reaction may be carried out under atmospheric pressure or under excess pressure of up to 6 bar. Atmospheric pressure is preferred.

The reaction time (for step (i)) differs with the reaction parameters but is generally between 1 h and 24 h.

In order to improve overall yield and enhance selectivity of the reaction, i.e. to reduce formation of the undesired dibromo and tribromo byproducts, it is preferred to carry out the reaction only up to a conversion of 5 to 60% (based on the amount of compound (II)), preferably 30 to 55%. In one preferred embodiment the reaction is carried out up to a conversion of about 50% (based on compound (II)). The degree of conversion may be checked by standard methods known to those skilled in the art, e.g. by HPLC analysis. When the desired degree of conversion is reached the reaction is stopped and the phases are separated.

The organic phase, containing the product of step (i), compound (III), unreacted starting material (I) and the dibromo and tribromo byproducts, may be extracted with water to remove water soluble impurities like acids and bromide. Product (III) can be isolated by known procedures, it is preferred, however, to use the organic phase without further workup for the reaction with the tertiary amine Q (step (ii)).

It is also possible to extract the aqueous phase with the organic solvent and to combine the organic phases in order to increase the yield of compound (III).

In step (ii) of the reaction compound (III) is reacted with a tertiary amine Q to obtain the ammonium compound (I).

Preferred tertiary amines Q follow from the preferred meanings of Q in formula (I), i.e., pyridine and tertiary alkyl amines $NR^9R^{10}R^{11}$, where $R^9$, $R^{10}$ and $R^{11}$ are each independently $C_1$-$C_4$ alkyl, or $R^9$ and $R^{10}$, when taken together, form a 5- or 6-membered ring in which $R^9R^{10}$ is represented by the structure: —$(CH_2)_n$—, optionally interrupted by O, S or $NR^{12}$, where n is an integer of 3, 4, or 5, provided $R^{11}$ is $C_1$-$C_4$ alkyl, and $R^{12}$ is $C_1$-$C_4$ alkyl.

Trimethylamine ($NMe_3$), and pyridine are particularly preferred.

Generally an excess of tertiary amine is used. Typically 1.05 to 2, preferably 1.05 to 1.5 equivalents of tertiary amine per equivalent of compound (II) are employed.

Generally the tertiary amine or the pyridine, optionally dissolved in a solvent, is slowly added to the solution of compound (II), whereupon the salt (I) forms and precipitates. In case of the preferred amine $NMe_3$, which is gaseous at room temperature, it is preferred to work in a closed vessel and charge the gaseous amine or the liquified amine under pressure to the solution of compound (III).

Step (ii) is preferably carried out at a temperature of about 0° C. to 70° C., more preferably 5° C. to 70° C., particularly preferred 5° C. to 55° C. The reaction can be carried out at ambient pressure or at elevated pressure. In a preferred embodiment, the reaction is carried out in a closed vessel at the pressure of the solvent and/or amine building up at the reaction temperature.

Work up of the reaction mixture and isolation of the ammonium compound (I) can be carried out by conventional methods, e.g. compound (I) can be filtered off.

In a preferred embodiment water is added to the reaction mixture to dissolve the product, compound (I), and aqueous phase and organic phase are separated. The water phase may be further extracted with organic solvent in order to increase the purity of the product (I), and to increase the yield of recovered starting material (II) in the organic phase. The amount of water must be sufficient for an aqueous phase to form and is preferably chosen to form a 20 to 45% by weight solution of compound (I) in the aqueous phase.

Ammonium compound (I) can be isolated from the aqueous phase by known methods. In a preferred embodiment compound (I) is not isolated and the aqueous phase obtained from step (ii) is used in subsequent reactions without further workup. In a further preferred embodiment the aqueous phase is mixed with a solvent that forms an azeotrope with water, e.g. toluene, and water is removed by azeotropic distillation. The resulting suspension of compound (I) can be used for further reactions.

In a further preferred embodiment of the invention, after separation of compound (I), the organic phase from step (ii) containing up to 80% of starting material (II) (based on the original amount used in step (i)) is recovered and recycled in the reaction process of step (i). Preferably further starting material (II) is added to compensate for the amount converted in previous step (i). Thus, in principle, the organic phase of step (i) can be recycled any amount of times, however, due to an accumulation of byproducts, mainly the di- and tribromination product of compound (II), up to 20, preferably up to 10 cycles are generally feasible.

In a preferred embodiment of the cyclic reaction process no additional starting material (II) is added in the last cycle to improve the overall yield and conversion rate.

In a further embodiment of the cyclic reaction process a certain amount of the organic phase, preferably about 5 to 20% by weight, are removed to reduce or suppress accumulation of byproducts in the organic phase. In this embodiment of the invention there is virtually no limit to the number of cycles in which the organic phase can be used.

The compounds of formula (I) are valuable intermediates in organic synthesis. They are especially useful for conversion to methoxymethyl compounds (IV) and further to herbicidal imidazolinone compounds (V).

In one aspect of the invention there is provided a process for producing compounds of formula (IV) comprising the steps of:

(i)/(ii) preparing a 5,6-disubstituted-3-pyridylmethyl ammonium bromide of the formula (I) as described above, and (iii) reacting the compound of formula (I) in methanol, toluene or a methanol/toluene mixture with a base selected from $MOCH_3$ and MOH (if the solvent comprises methanol), where M is as defined in formula (IV).

In one preferred embodiment, where $Y^2$ is OM, step (iii) is carried out as disclosed in EP-A 0 747 360, i.e. by reaction of the respective compound of formula (I) in methanol with a base.

Bases suitable for use in this embodiment of invention are alkaline metal or alkaline earth metal hydrides, hydroxides, carbonates or $C_1$-$C_4$ alkoxides, preferably sodium or potassium hydroxide or alkoxide. Suitable alkaline metals are sodium or potassium. Suitable alkaline earth metals are calcium, magnesium and the like. Alkaline metals such as sodium or potassium are preferred.

Suitable reaction temperatures are about 120° to 180° C., preferably about 120° to 150° C. Reaction pressures would be those pressures which normally accompany heating a solvent in a closed reaction system to a temperature range above its boiling point.

Compounds of formula (IV) where $Y^2$ is OH may be obtained by acidification of the respective dicarboxylates.

In a further preferred embodiment, where $Y^2$ is $OCH_3$ or OH, step (iii) is carried out as disclosed in EP-A 0 548 532, i.e. by reacting compound (I) with $MOCH_3$, where M is an alkaline metal such as Na or K, in the presence of an organic solvent preferably at a temperature range of 0° C. to 110° C. to form a first mixture further reacting said first mixture with at least 2.0 molar equivalents of an aqueous base preferably at a temperature range of about 20° C. to 120° C. to form a second mixture and adjusting the pH of said second mixture to a value below 2.5 with an acid to form acid compounds of formula (IV).

Aqueous bases suitable for use in this embodiment of the invention include aqueous sodium hydroxide solution, aqueous potassium hydroxide solution and the like. Acids that may be used in the method of the invention include mineral acids such as sulfuric acid, hydrochloric acid and the like.

Organic solvents that may be used in the method of the invention include acetonitrile, tetrahydrofuran, aromatic hydrocarbons, methanol and the like. The preferred inert organic solvent is methanol.

In another preferred embodiment, where $Y^2$ is $OCH_3$, step (iii) is carried out as disclosed in EP-A 0 548 532, and the compound of formula (I) is reacted with $MOCH_3$, where M is Na or K, in an inert solvent, preferably methanol.

Further conversion of compound (IV) to herbicidal imidazolinones (V) can be achieved by methods known in the art.

Methods that may be used to create the imidazolinone herbicides are illustrated in the book "The Imidazolinone Herbicides" edited by D. L. Shaner and S. L. O'Connor, published 1991 by CRC Press, Boca Raton, Fla. with particular reference to Chapter 2 entitled "Synthesis of The Imidazolinone Herbicides", pages 8-14 and the references cited therein. The following patent literature references also illustrate the methods that may be used to convert the pyridine diacids, esters and salts to the imidazolinone final products:

U.S. Pat. Nos. 5,371,229; 5,250,694; 5,276,157; 5,110,930; 5,122,608; 5,206,368; 4,925,944; 4,921,961; 4,959,476; 5,103,009; 4,816,588; 4,757,146; 4,798,619; 4,766,218; 5,001,254; 5,021,078; 4,723,011; 4,709,036; 4,658,030; 4,608,079; 4,719,303; 4,562,257; 4,518,780; 4,474,962; 4,623,726; 4,750,978; 4,638,068; 4,439,607; 4,459,408; 4,459,409; 4,460,776; 4,125,727 and 4,758,667, and EP-A-0 041 623.

In one embodiment the conversion of compound (IV) to a herbicidal imidazolinone (V) is carried out in analogy to the method disclosed in EP-A 0 233 150 or B. I. Quang et al., Modem Agrochemicals 6 (2007) p. 14.

In this embodiment a herbicidal imidazolinone compound (V) is prepared by (i)/(ii)/(iii) preparation of a compound (IV), as outlined above, and (iv) reacting compound (IV) in the presence of a strong base with an 2-aminoalkane carboxamide of formula (VI),

where $R^4$ and $R^5$ are as in formula (V),
and adjusting the pH to give a compound of formula (V).

The reaction is carried out in an inert solvent, e.g. aromatic hydrocarbons and halogenated hydrocarbons, such as toluene, alcohols, such as methanol or tert-butanol. Water immiscible solvents are preferred. Suitable strong bases are alkaline metal alcoholates and alkali metal hydroxides, such as $NaOCH_3$ or $KO\text{-}tert\text{-}C_4H_9$. The reaction is carried out in the range of from room temperature (generally 22° C.) to reflux temperature of the reaction mixture, preferably 50 to 90° C.

In further embodiments of the invention conversion of compound (IV) to a herbicidal imidazolinone (V) is carried out in analogy to the methods described in EP-A 0 041 623, U.S. Pat. No. 4,518,780 or EP-A 0 144 595.

According to these embodiment compound (IV) is first converted to the respective anhydride by known methods, such as reaction with acetic anhydride.

In one embodiment compound (V) is prepared by
(i)/(ii)/(iii) preparation of a compound (IV) as outlined above;
(iv-1) conversion of compound (IV) to the anhydride (VII),

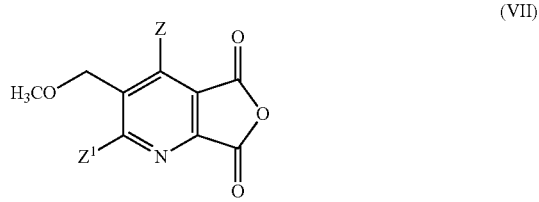

(iv-2) reacting anhydride (VII) with an 2-aminoalkane carboxamide of formula (VI),

to yield amide (VIII),

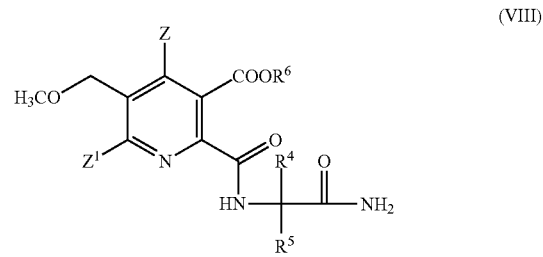

and (iv-3) condensation of amide (VIII) to yield the herbicidal imidazolinone (V).

Steps (iv-2) and (iv-3) may be carried out as a one-pot reaction.

In one embodiment step (iv-2) is carried out in analogy to the procedure disclosed in example 10 of EP-A 0 322 616. Compound (IV), a substituted 2-aminoalkane carboxamide (VI) and a tertiary amine, preferably triethylamine are reacted in a polar aprotic solvent, such as acetonitrile, to yield an ammonium salt (VIII) ($R^6$=$HNR_3$), which can be acidified to an acid (VIII) ($R^6$=H).

Alternative procedures are disclosed in U.S. Pat. No. 4,518,780 and EP-A 0 144 595. In the latter document the addition of a nitrogen base selected from pyridine, the picolines, quinoline and lutidine is disclosed to improve the regioselectivity of the reaction, i.e. to increase the amount of 2-addition product.

In one embodiment of step (iv-3) amido compound (VIII), preferably in the form of an ammonium salt ($R^6$ is $HNR_3$), is reacted with an alkaline metal methoxide, preferably $NaOCH_3$ in methanol in analogy to example 11 of EP 0 322 616. The resulting suspension is held at reflux until complete conversion. After cooling the mixture is acidified to obtain compound (III) either as the ammonium salt (acidification to a pH of about 4) or the free acid (acidification to pH≤2).

In a further preferred embodiment, the reaction mixture from step (iv-2) is reacted with methanol (generally 2 to 100 equivalents based on (VIII)) in the presence of an aqueous base (generally 3 to 100 equivalents based on (VIII)), the base being preferably selected from MOH and $MOCH_3$, where M is an alkaline metal, preferably Na or K, particularly Na.

The reaction is carried out at a temperature in the range of from 20 to 120° C., preferably 40 to 90° C. The reaction can be carried out at atmospheric pressure or at elevated pressure, preferably the pressure forming at the desired reaction temperature. The reaction time is generally from 1 to 8 h, preferably from 1 to 5 h.

Isolation of product (V) can be achieved by standard methods. In a preferred embodiment water is added and organic solvents are distilled off. The residue can be taken up in water and acidified, whereupon compound (V) precipitates. After filtration the crude product can be further purified, e.g. by stirring with water or recrystallization.

In a further embodiment compound (V) is prepared by
(i)/(ii)/(iii) preparation of a compound (IV) as outlined above;
(iv-1) conversion of compound (IV) to the anhydride (VII),

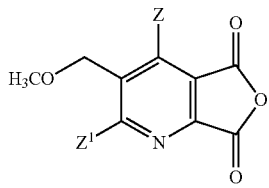

(iv-2) reacting anhydride (VIII) with aminocarbonitrile (IX), $$H_2N—CR^4R^5—CN \quad (IX)$$

where $R^4$ and $R^5$ are as in formula (V),
to obtain amidonitrile compound (X),

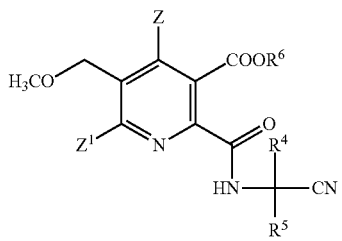

where the symbols are as in formula (V) and $R^6$ is preferably H, (iv-3) hydrolysis of the nitrile group in compound (X) to yield amide (VIII),

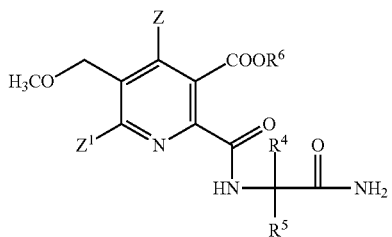

where the symbols have the same meaning as in formula (V) and $R^6$ is preferably H, and (iv-4) condensing amide (VIII) to yield the herbicidal imidazolinone (V).

Preparation of the anhydride can be carried out as described above.

Aminonitriles (IX), which are employed in step (iv-2), are commercially available or can be prepared by methods known in the art. Generally 0.8 to 1.2 equivalents aminonitrile (IX) per equivalent of compound (IV) are used, preferably 0.95 to 1.1.

The reaction is carried out in a solvent, which is preferably selected from aromatic hydrocarbons, preferably toluene, mesitylenes, chlorinated aromatic hydrocarbons, such as chlorobenzene, dichlorobenzene, chlorinated hydrocarbons, such as 1.2-dichloroethane, dichloromethane, acetic acid, and mixtures thereof.

If acetic acid is not used as the main solvent, addition of 0.5 to 4 equivalents, preferably 1 to 3 equivalents (based on compound (I)), is advantageous. Further advantageous additives that improve the selectivity of the ring-opening reaction (2 versus 3 position) are listed in EP-A 0 144 555, and comprise pyridine, 4-picoline, 2-picoline and quinoline.

The reaction is generally carried out at a temperature range of from about 40 to about 120° C., preferably of from about 60 to about 100° C. The reaction time is generally from about 1 to about 3 h.

In a preferred embodiment compound (IV) is dissolved in the solvent and brought to the reaction temperature, and aminonitrile (IX) is gradually added. After completion of the reaction and cooling, nitrile compound (X) can be isolated by standard methods.

In a preferred embodiment, however, compound (X) is not isolated but the reaction mixture is directly used in the following hydrolyzation step of the nitrile (step iv-3).

In a typical procedure a slight excess (e.g. 1.1 to 1.5 equivalents based on (IX)) of a strong mineral acid, preferably sulfuric acid (preferably in a concentration of 30 to 98%) and water (e.g. 2 to 10 equivalents) are added at a temperature which is generally in the range of about 30° C. to 120° C., preferably 50° C. to 90° C. The mixture is further stirred until complete conversion. The reaction time is generally from 1 to 8 h, preferably 1 to 5 h.

Workup and isolation of amide (VIII) can be achieved by standard methods, such as an aqueous solution (e.g. as its ammonium salt). In a preferred embodiment the reaction mixture is directly used in the following condensation step (iv-4).

In an alternative embodiment hydrolysis of the nitrile group is effected by reaction with aqueous $NaOH/H_2O_2$ as disclosed, e.g. in EP-A 0 144 595 and U.S. Pat. No. 4,518,780.

Condensation of amido compound (X) to the herbicidal imidazolinone may be carried out as described above.

All of the above processes are particularly preferred for the preparation of the compound of formula (V) where Z and $Z^1$ are H, $R^6$ is H, $R^4$ is $CH_3$ and $R_5$ is $CH(CH_3)_2$, i.e. imazamox.

The invention is illustrated by the following examples without limiting it thereby.

EXAMPLES

Example 1

Synthesis of [(5,6-dicarboxy-3-pyridyl)methyl]trimethylammonium bromide, dimethylether (Ia)

a) Synthesis of dimethyl 5-(bromomethyl)-2,3-pyridinedicarboxylate (IIIa) (50% conversion)

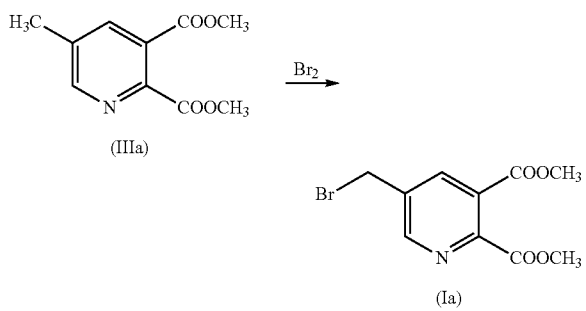

218.4 g (1.0 mol) compound (IIa) were dissolved in 1139.0 g 1,2-dichloroethane (EDC) and 160.0 g water were charged and heated to 72° C. (about 1-2° C. below reflux). 14.4 g (0.075 mol) 2,2'-azobis(2-methylbuty-ronitrile) (Vazo 67) in 160.0 g EDC were added over 2 h at 72° C. After 30 minutes 143.8 g (0.9 mol) bromine were added over 2 h, under pH control (pH 5-7) by dosage of about ca. 375.0 g aqueous NaOH (15%). The mixture was stirred over 1 h for reaction completion (HPLC assay). After cooling to 40° C. the phases were separated.

b) Synthesis of Compound (Ia)

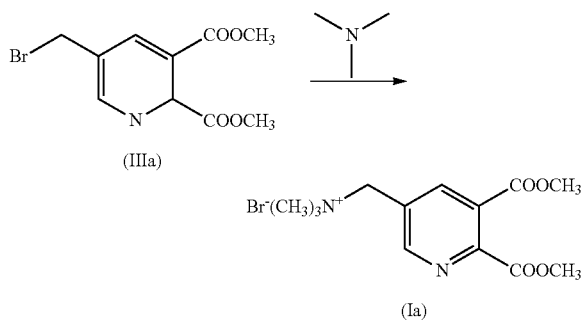

288.1 g (1.0 mol) compound (IIIa) in mixture with di- and tribromination byproducts) in 3359.0 g EDC (organic phase from step a, including unreacted compound (IIa) and higher brominated byproducts) were charged. The mixture was heated to 30° C. and the vessel evacuated to 200 mbar. 70.9 g (1.2 mol) trimethylamine (TMA) was added to the gas phase during 2 h at 40° C. (closed system). The mixture was stirred 1 additional hour (HPLC conversion check: compound (IIIa) in solution <0.1%).

Excess TMA was distilled off together with EDC (mass: 40% of the EDC mass transferred to step 2 (1344 g) at 50-55° C. (370-250 mbar). The pH of the distillate was <9. 630.0 g water was sprayed to the wall so that the solid is dissolved and the mixture was transferred to the next vessel. The mixture was then stirred 0.25 h, and the lower organic phase was separated at 40° C. 320.4 g EDC were added. The mixture was stirred and the lower organic phase was separated at 40° C. The back extraction was repeated (40° C.) with 320.4 g EDC. The two organic back extraction phases were combined with the first organic phase and recycled to the next bromination batch (after addition of 50% fresh compound (IIa) for a further cycle.

Steps a) and b) were repeated six times. In the last cycle no compound (IIa) was added in step a) and 0.8 mol TMA were added in step b).

The overall conversion rate of compound (IIa) was 96.6%. The yield of compound (Ia) (over 7 cycles) was 77.4% at a purity of >95% (as determined by HPLC).

Example 2

Synthesis of [(5,6-dicarboxy-3-pyridyl)methyl]trimethylammonium bromide, dimethylether (Ia)

The synthesis was carried out as in example 1, except that in step (a) the full amount of 13.65 g (0.071 mol) 2,2'-azobis (2-methylbutyronitrile) (Vazo 67) in 160.0 g EDC was added at 72° C., and after 5 minutes 135.8 g (0.85 mol) bromine were added over 2 h, under pH control (pH 5) by dosage of about 375.0 g aqueous NaOH (15%).

The overall conversion rate of compound (IIa) was 96.6%. The yield of compound (Ia) (over 7 cycles) was 78.2% at a purity of >95% (as determined by HPLC).

Example 3

Synthesis of [(5,6-dicarboxy-3-pyridyl)methyl]pyridinium bromide, dimethylether

Step (a) was carried out according to the procedure of example 1.

Synthesis of compound (Ib)

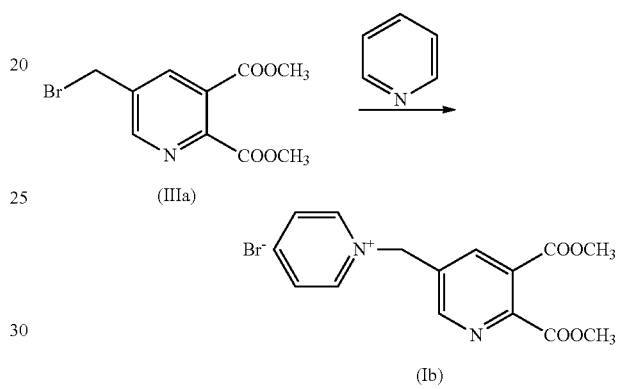

82.4 g (0.286 mol) compound (IIIa) in mixture with di- and tribromination byproducts) in EDC (1183.8 g organic phase from step a, including unreacted compound (IIa) and higher brominated byproducts) were charged. The mixture was heated to 40° C. 27.88 g (0.292 mol) pyridine was added dropwise over 60 min. at 40° C. The mixture was stirred at 55° C. for one additional hour.

Excess pyridine was distilled off together with EDC at 55-60° C. under vacuum (~90 torr) until the total weight of the mixture was 382.7 g. 134.8 g of water were added. The mixture was stirred for 15 min. and was then allowed to settle and split for 15 min. The phases were separated and analyzed.

The yield of compound (Ib) for one conversion was 73.4% (based on the moles monobromo compound (IIIa) converted).

Example 4

Preparation of dimethyl 5-(methoxymethyl)-2,3-pyridinedicarboxylate (according to ex. 7 of EP-A 0 548 532)

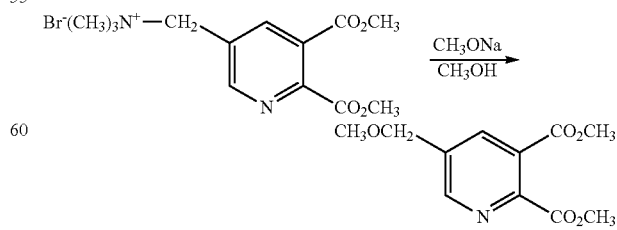

A mixture of 25% sodium methoxide in methanol (320.0 g, 1.5 mol) and [(5,6-dicarboxy-3-pyridyl)-methyl]trimethylammoniumbromide, dimethyl ester (160.0 g, 0.5 mol) in methanol (630 ml) is heated at reflux for 6 hours under nitrogen. The reaction mixture is cooled to 5° C. and acetic acid (90 g) and water (200 ml) are added. Methanol is removed in vacuo, water is added and the mixture is extracted with methylene chloride.

Example 5

Preparation of 5-(methoxymethyl)-2,3-pyridinedicarboxylic acid (according to ex. 8 of EP-A 0 548 532)

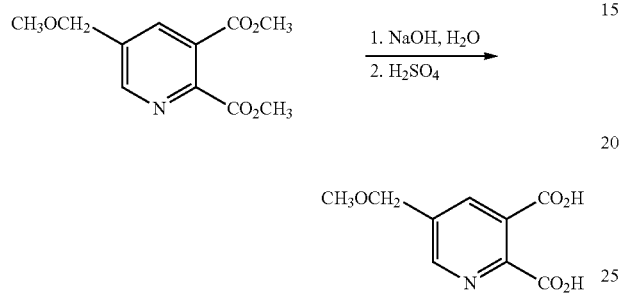

A mixture of dimethyl 5-(methoxymethyl)-2,3-pyridinedicarboxylate (60.0 g, 0.25 mol) and 50% sodium hydroxide solution (50.0 g, 0.63 mol) in water is heated at 90-110° C. for 2 hours under nitrogen while distilling off methanol and water. The reaction mixture is cooled to 10° C., treated with sulfuric acid to adjust the pH to 2.0 and filtered to obtain a solid. The solid is washed with water and vacuum dried to give the title product as a white solid (44.3 g, mp 161-162° C.).

Example 6

Preparation of 5-(methoxymethyl)-2,3-pyridinedicarboxylic acid (according to ex. 3 of EP-A 0 548 532)

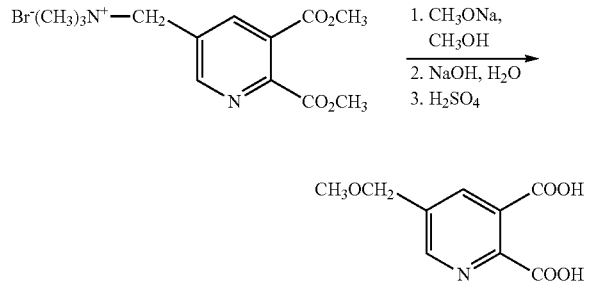

A mixture of 25% sodium methoxide in methanol (270 g, 1.25 mol) and [(5,6-dicarboxy-3-pyridyl)-methyl]trimethylammonium bromide, dimethyl ester (Ia) (347 g, 1.00 mol) in methanol (650 ml) is heated at reflux for 1 hour under nitrogen. Water (1 l) and sodium hydroxide (80.0 g, 2.0 mol) are added and the reaction mixture is distilled until the pot is 100-105° C. The reaction mixture is cooled to room temperature, treated with sulfuric acid to adjust the pH to a value from 1.5 to 2 and filtered to obtain a solid. The solid is washed with water and dried in a vacuum oven to obtain the title product as a white solid (mp 161-162° C.) which is greater than 99% pure by HPLC analysis.

Example 7

Preparation of disodium 5-(methoxymethyl)pyridine-2,3-dicarboxylate from disodium [5,6-(dicarboxylate-3-pyridyl)methyl]trimethylammonium bromide (according to ex. 3 of EP-A 0 747 360)

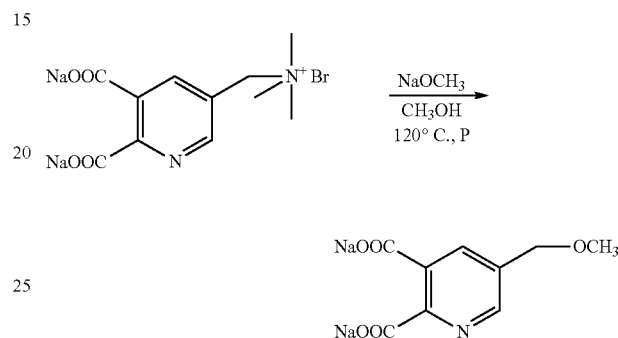

A mixture of disodium [(5,6-dicarboxylate-3-pyridyl)methyl]trimethylammonium bromide (5.0 g, 13.8 mmol) and a 25% wt/wt solution of sodium methoxide in methanol (4.46 g, 20.7 mmol of $NaOCH_3$) in 75 g of methanol is heated at 120° C. for 21 hours in a pressure reactor. The reaction is cooled to room temperature, treated with water and concentrated to a final weight of 55.03 g. A 5.0 g sample is assayed by LC analysis (30% $CH_3CN$, 0.77 M $H_3PO_4$). The remainder of the reaction solution is evaporated to dryness to give a solid residue, identified by NMR analysis.

The invention claimed is:
1. A process for manufacturing a compound of formula (I),

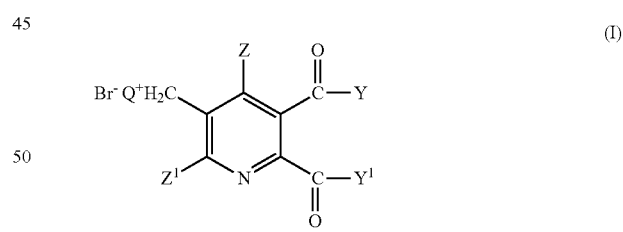

wherein
Q$^+$ is a tertiary aliphatic or cyclic, saturated, partially unsaturated or aromatic amine;
Z is hydrogen or halogen;
Z$^1$ is hydrogen, halogen, cyano or nitro;
Y and Y$^1$ are each independently OR$^1$, NR$^1$R$^2$, or when taken together YY$^1$ is —O—, —S— or NR$^3$—;
R$^1$ and R$^2$ are each independently hydrogen,
$C_1$-$C_4$ alkyl optionally substituted with $C_1$-$C_4$ alkoxy or phenyl optionally substituted with one to three $C_1$-$C_4$ alkyl groups, $C_1$-$C_4$ alkoxy groups or halogen atoms, or phenyl optionally substituted with one to three $C_1$-$C_4$ alkyl groups, $C_1$-$C_4$ alkoxy groups or halogen atoms;

$R^3$ is hydrogen or $C_1$-$C_4$ alkyl;

comprising (i) reacting a compound of formula (II),

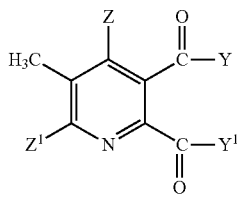
(II)

with bromine in the presence of a radical initiator in a solvent mixture comprising an aqueous phase and an organic phase, where the organic phase comprises a solvent selected from the group consisting of 1,2-dichloroethane, 1,2-dichlorobenzene, 1,3-dichlorobenzene, and 1,4-dichlorobenzene, and wherein the pH-value of the aqueous phase is from 3 to <8, to obtain a compound of formula (III),

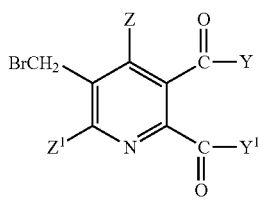
(III)

and (ii) reacting the compound of formula (III) with a tertiary amine base Q in a solvent at a temperature range of 0° C. to 100° C. to obtain a compound of formula (I).

2. The process as claimed in claim 1, where the organic solvent in step (i) is 1,2-dichloroethane.

3. The process as claimed in claim 1, where -Q⁺ in formula (I) is

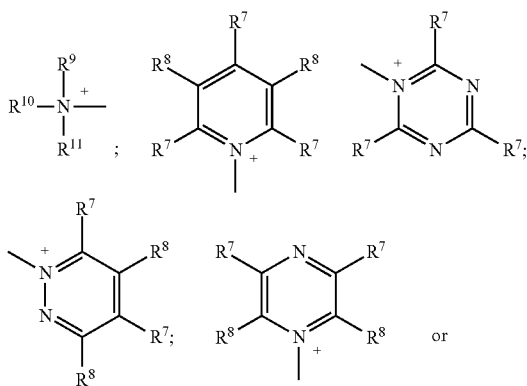

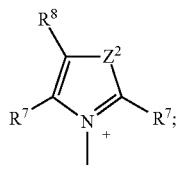

$Z^2$ is O, S or $NR^{12}$;

$R^{12}$ is $C_1$-$C_4$ alkyl; and $R^7$ and $R^8$ are each independently hydrogen, halogen, $C_1$-$C_4$ alkyl or $C_1$-$C_4$ alkoxy, or $R^7$ and $R^8$, when taken together, form a 5- or 6-membered saturated or unsaturated ring optionally interrupted by O, S, or $NR^{12}$ and optionally substituted with one to three halogen atoms, $C_1$-$C_4$ alkyl groups or $C_1$-$C_4$ alkoxy groups, and where $R^9$, $R^{10}$ and $R^{11}$ are each independently $C_1$-$C_4$ alkyl, or $R^9$ and $R^{10}$, when taken together, form a 5- or 6-membered ring in which $R^9R^{10}$, is represented by the structure: —$(CH_2)_n$—, optionally interrupted by O, S or $NR^9$, where n is an integer of 3, 4 or 5, provided $R^{11}$ is $C_1$-$C_4$ alkyl.

4. The process as claimed in claim 1, where the compound of formula (I) is the compound of formula (Ia):

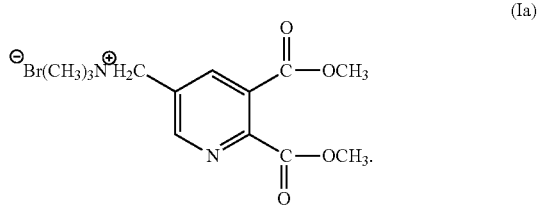
(Ia)

5. The process as claimed in claim 1, where the reaction in step (i) is carried out up to a conversion of compound (II) of 20 to 60%.

6. The process as claimed in claim 1, where the organic phase in step (ii) is recycled in step (i) with optional addition of compound (II).

7. The process as claimed in claim 1, where the pH-value of the aqueous phase in step (i) is from 3 to 7.

8. The process as claimed in claim 1, where the initiator in step (i) is selected from the group consisting of azobisisobutyronitrile, 2,2'-azobis(2-methylbutanenitrile), 2,2'-azobis(2,4-dimethyl-pentanenitrile and 1,1'-azobis(cyclohexanecarbonitrile).

9. The process as claimed in claim 1, where the molar ratio of the compound of formula (II) to bromine in step (i) is 1:0.5-1.2.

10. The process as claimed in claim 1, where step (i) is carried out at a temperature of 50° C. to 120° C.

11. The process as claimed in claim 1, where the tertiary amine Q in step (ii) is trimethylamine.

12. The process as claimed in claim 1 further comprising (iii) reacting the compound of formula (I) in methanol, toluene or a methanol/toluene mixture with a base selected from the group consisting of $MOCH_3$ and MOH, where M is an alkaline metal or an alkaline earth metal, to form a compound of formula (IV),

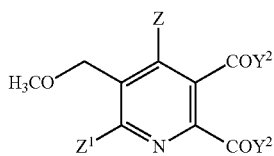

(IV)

where

Z is hydrogen or halogen;

$Z^1$ is hydrogen, halogen, cyano or nitro;

$Y^2$ is $OCH_3$ or OM.

13. The process as claimed in claim 12 further comprising (iv) converting the compound of formula (IV) into a compound of formula (V),

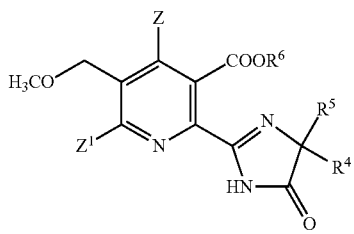

(V)

wherein

Z is hydrogen or halogen;

$Z^1$ is hydrogen, halogen, cyano or nitro;

$R^4$ is $C_1$-$C_4$ alkyl;

$R^5$ is $C_1$-$C_4$ alkyl, or $C_3$-$C_6$ cycloalkyl, or $R^4$ and $R^5$ taken together with the atom to which they are attached form a $C_3$-$C_6$ cycloalkyl group optionally substituted with methyl, and $R^6$ is hydrogen;

a group of the formula (lower alkyl)$_2$;

$C_1$-$C_{12}$ alkyl optionally substituted with one of the following groups: $C_1$-$C_3$ alkoxy, halogen, hydroxyl, $C_3$-$C_6$ cycloalkyl, benzyloxy, furyl, phenyl, halophenyl, lower alkylphenyl, lower alkoxyphenyl, nitrophenyl, carboxyl, lower alkoxycarbonyl, cyano or tri lower alkylammonium;

$C_3$-$C_{12}$ alkenyl optionally substituted with one of the following groups:

$C_1$-$C_3$ alkoxy, phenyl, halogen or loweralkoxycarbonyl or with two $C_1$-$C_3$ alkoxy groups or two halogen groups; or $C_3$-$C_6$ cycloalkyl optionally substituted with one or two $C_1$-$C_3$ alkyl groups;

or a cation.

14. The process as claimed in claim 13, further comprising (iv-1) optionally preparing the anhydride (VII) of compound (IV);

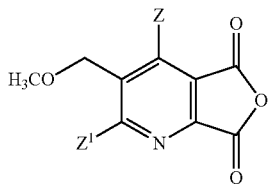

(VII)

(iv-2) reacting compound (IV) or its anhydride (VII) in the presence of a base with an 2-aminoalkane carboxamide of formula (VI), $H_2N—CR^4R^5—CONH_2$ (VI)

where $R^4$ and $R^5$ are as in formula (V).

15. The process as claimed in claim 13, further comprising (iv-1) converting compound (IV) to the anhydride (VII);

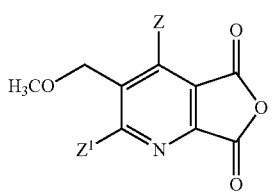

(VII)

(iv-2) reacting anhydride (VII) with aminocarbonitrile (IX), $H_2N—CR^4R^5—CN$ (IX)

where $R^4$ and $R^5$ are as in formula (V), to obtain amidonitrile compound (X),

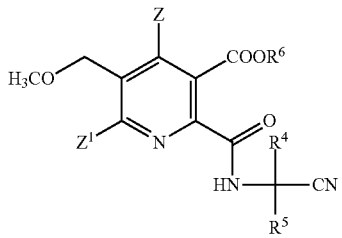

(X)

wherein $R^6$ is H;

(iv-3) hydrolyzing the nitrile group in compound (X) to yield amide (VIII),

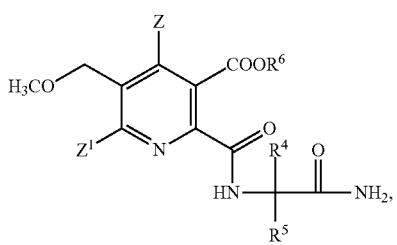

(VIII)

and (iv-4) condensing amide (VIII) to yield the herbicidal imidazolinone (V).

* * * * *